United States Patent [19]

Moncada et al.

[11] Patent Number: 5,585,402

[45] Date of Patent: Dec. 17, 1996

[54] NITRIC OXIDE SYNTHASE INHIBITORS

[75] Inventors: Salvador E. Moncada; Richard M. J. Palmer, both of Beckenham, England

[73] Assignee: Glaxo Wellcome Inc., Research Triangle Park, N.Y.

[21] Appl. No.: 452,367

[22] Filed: May 26, 1995

Related U.S. Application Data

[63] Continuation of Ser. No. 997,291, Dec. 23, 1992, abandoned.

[51] Int. Cl.$^6$ .................................................. A61K 31/195
[52] U.S. Cl. ........................................... 514/564; 514/565
[58] Field of Search ................................. 514/564, 565

[56] References Cited

U.S. PATENT DOCUMENTS

| | | | |
|---|---|---|---|
| 4,282,217 | 8/1981 | Baglioni et al. | 424/240 |
| 5,028,627 | 7/1991 | Kilbourn et al. | 514/565 |
| 5,081,148 | 1/1992 | Braquet et al. | 514/162 |
| 5,158,883 | 10/1992 | Griffith | 435/240.2 |
| 5,356,873 | 10/1994 | Mark et al. | 514/2 |

FOREIGN PATENT DOCUMENTS

| | | |
|---|---|---|
| A10230037 | 7/1987 | European Pat. Off. . |
| WO91/04023 | 4/1991 | WIPO . |
| WO93/00893 | 1/1993 | WIPO . |

OTHER PUBLICATIONS

CA 118:78331, Nava et al., 1992.
Tissue injury caused by depostion of immune complexes is L–arginine dependent; vol. 88 pp. 6338–6342, Jul. 1991; Medical Sciences; Michael S. Mulligan et al.
Beckman, J. S. The double–edged role of nitric oxide in brain function and superoxide–mediated injury. J. Dev. Physiol. (Eynsham). 15: 53–60, 1991.
Li, L. et al. Role of nitric oxide lysis of tumor cells by cytokine–activated endothlial cells. Cancer Res. 51: 2531–2535, 1991.
Nakaki, T. et al. Inhibition by nitric oxide and nitric oxide–producing vasodilators of DNA synthesis in vascular smooth muscle cells. Eur. J. Pharmacol. Mol. Pharmacol. Sect. 3: 347–353, 1990.
Boughton Smith, N. K. et al. Protective effect of S–nitroso–N–acetyl–penicillamine in endotoxin–induced acute intestinal damage in the rat. Eur. J. Pharmacol. 191: 485–488, 1990.
Hutcheson, I. R. et al. Role of nitric oxide in maintaining vascular integrity in endotoxin–induced acute intestinal damage in the rat. Br. J. Pharmacol. 101: 815–820, 1990.
Kilbourn, R. G. et al. Reversal of Endotoxin–mediated shock by $N^G$–methyl–L–arginine, an inhibitor of nitric oxide synthesis. Biochem. Biophys. Res. Comm. 172(3): 1132–1138, 1990.
Marshall, J. J. et al. Endothelium–derived relaxing factors. A perspective from in vivo data. Hypertension 16: 371–386, 1990.

Rubanyi, G. M. et al. Cytoprotective function of nitric oxide inactivation of superoxide radicals produced by human leukocytes. Biochem. Biophys. Res. Commun. 181: 1392–1397, 1991.
Palmer, R. M. J. et al. The role of ntric oxide in endothelial cell damage and its inhibition by glucocorticoids. Br. J. Pharmacol. 105: 11–12, 1992.
Wright, C. E. et al. Protective and pathological roles of nitric oxide in endotoxin shock. Cardiovasc. Res. 26: 48–57, 1992.
Ialenti, A. et al. Modulation of acute inflammation by endogenous nitric oxide. Eur. J. Pharmacol. 211: 177–182, 1992.
Bergmann, L. et al. Cytotoxic action of IL–1B against pancreatic islets is mediated via nitric oxide formation and is inhibited by $N^G$–monomethyl–L–arginine. Febs (Fed. Eur. Biochem. Soc.). Lett. 299: 103–106, 1992.
Langrehr, J. M. et al. Evidence that nitric oxide production by in–vivo allosensitized cells inhibits the development of allospecific CTL. Transplantation (Baltimore) 53:632–640, 1992.
Demerle Pallardy, C. et al. Absence of implication of L–arginine/nitric oxide pathway on neuronal cell injury induced by L–glutamate or hypoxia. Biochem. Biophys. Res. Commun. 181: 456–464, 1991.
Billiar, T. R. et al. Modulation of nitrogen oxide synthesis in vivo: $N^G$–monomethyl–L–arginine inhibits endotoxin–induced nitrite/nitrate biosynthesis while promoting hepatic damage. J. Leuk. Biol. 48: 565–569, 1990.
Ochoa, J. B. et all. Nitrogen oxide levels in patients after trauma and during sepsis. Ann. Surg. 214: 621–626, 1991.
Bone, R. C. The pathogenesis of sepsis. Ann. Intern. Med. 115:457–469, 1991.
Dal Nogare, A. R. Septic shock. Am. J. Med. Sci. 302: 50–65, 1991.
Nava, E. et al. The role of nitric of nitric oxide in endotoxic shock. (Corresponds to the poster). (1991).
Rees, D. D. et al. A specific inhibitor of nitric oxide formation from L–arginine attenuates endothelium–dependent relaxation. Br. J. Pharmacol. 96: 418–424, 1989.
Sakuma, I. et al. Identification of arginine as a precursor of endothlium–derived relaxing factor. Proc. Natl. Acad. Sci. USA. 85: 8664–8667, 1988.
Beckman, J. S. et al. Apparent hydroxyl radical production by peroxynitrite: Implications for endothelial injury from nitric oxide and superoxide. Proc. Natl. Acad. Sci. USA. 87: 1620–1624, 1990.
Beckman, J. S. Ischaemic injury mediator. Nature 345: 27–28, 1990.

(List continued on next page.)

*Primary Examiner*—Kimberly Jordan
*Attorney, Agent, or Firm*—George W. Neuner

[57] ABSTRACT

The present invention discloses a method for inhibiting tissue damage in mammals caused by pathological NO production, which comprises administering an effective tissue damage inhibition amount of a NO synthase inhibitor to said mammal. Preferably the NO synthase inhibitor is L–NMMA.

8 Claims, 3 Drawing Sheets

OTHER PUBLICATIONS

Nava, E. et al. The role of nitric oxide in endotoxin shock. Deleterious effects of $N^G$–monomethyl–L–arginine and protective effects of dexmethasone. Poster presented at a meeting in the United Kingdom on The Biology of Nitrite Oxide (1991).

Proceeding Natl. Acad. Sci. USA; vol. 85; pp. 8664–8667; Nov. 1988; Sakuma et al.

Proc. Natl. Acd. Sci. USA: vol. 86: pp. 3375–3378 May 1989: D. D. Rees et al.

Dr. J. Pharmacal (1990), 101, pp. 746–752.

NITRIC OXIDE SYNTHASE INHIBITORS

This is a continuation of application Ser. No. 07/997,291 filed on Dec. 23, 1992, now abandoned.

The present invention relates to the use of nitric oxide synthase inhibitors in preventing tissue damage.

We have found that excess nitric oxide production in vascular endothelial cells causes cytotoxicity in these cells. Such excess NO production may be caused following expression of the inducible NO synthase by inflammatory mediators such as cytokines and bacterial toxins associated with septicaemia and other inflammatory or immunological reactions. It has been reported that increased NO production by macrophages, following induction of NO synthase, contributes to host defence against pathogens and tumour cells (it is cytotoxic or cytostatic for these cells) without being toxic to the macrophages. However, we have found that in endothelial cells induction of NO synthase is also cytotoxic, causing tissue damage to those cells. We have now found that it is this tissue damage that contributes most to mortality in conditions such as septicaemia.

Accordingly, the present invention provides a method for preventing tissue damage in mammals caused by pathological NO production which comprises the administration of an effective amount of an NO synthase inhibitor.

Suitably the NO synthase inhibitor is an arginine derivative such as those described in U.S. Pat. No. 5,028,627 and preferably it is L-NMMA.

L-NMMA is available from Sigma Chemical Company Limited, Fancy Road, Poole, Dorset BH17 7NH, England.

The ability of NO synthase inhibitors to prevent tissue damage may be demonstrated in-vivo by the inhibition of the appearance in the blood stream of cytosolic markers, such as alanine amino transferase and creatinine. These markers are intra-cellular substances which are released when the cell dies and disrupts.

As mentioned previously, tissue damage is a feature of excess NO production which in turn may be caused by septicaemia, inflammatory conditions and immunological reactions. Septicaemia is caused by microbial infections, e.g. bacterial, fungal and protozoal infections and by viral infections. It is particularly associated with meningococcal, staphylococal, streptococcal, Pseudomonas, clostridial infections. Accordingly, the present invention also provides a method for the prevention and/or treatment of septicaemia which comprises the administration of an effective amount of an NO synthase inhibitor optionally in conjunction with an antimicrobial agent.

Excess NO production may also arise from graft rejection, e.g. from transplant surgery, in which case the NO synthase inhibitor will normally be administered with an immunosuppressant, such as cyclosporin, azathioprine, or FK506. Accordingly, the present invention provides a method for the prevention of graft rejection which comprises the administration of an effective amount of an NO synthase inhibitor, optionally in conjunction with an effective amount of an immunosuppressant.

Selective NO synthase inhibitors could be used to prevent excess NO production in adult respiratory distress syndrome (ARDS), arthritis, myocarditis and other inflammatory indications in which an excess NO production contributes to the pathophysiology of the condition. The NO synthase inhibitor will normally be given in conjunction with an anti-inflammatory agent prescribed for the conditions. Accordingly, the present invention provides a method for the prophylaxis or treatment of inflammatory conditions in which excess NO production contributes to the pathophysiology which comprises the administration of an effective amount of an NO synthase inhibitor, optionally in conjunction with an effective amount of an anti-inflammatory agent.

Many NO synthase inhibitors, for example L-NMMA, are capable of forming salts. Thus, the present invention includes NO synthase inhibitors in the form of salts, in particular acid addition salts.

Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, p-toluenesulphonic, benzenesulphonic and isethionic acids. Salts of the compounds of NO-synthase inhibitors can be made by reacting the appropriate compound in the form of the free base with the appropriate acid.

Whilst it may be possible for the NO-synthase inhibitors to be administered as the raw chemical, it is preferable to present them as a pharmaceutical formulation. According to a further aspect, the present invention provides a pharmaceutical formulation comprising the NO synthase inhibitor or a pharmaceutically acceptable salt or solvate thereof, together with one or more pharmaceutically acceptable carriers therefor and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association the NO-synthase inhibitor or a pharmaceutically acceptable salt or solvate thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The NO synthase inhibitors of the invention may be administered orally or via injection at a dose of from 1 to 100 mg/kg per day. When the NO synthase inhibitors are given by injection, this will normally be in the form of an intravenous bolus or by infusion, preferably the latter. The dose range for adult humans is generally from 70 mg to 2.5 g/day and preferably 150 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

L-NMMA is preferably administered by injection, conveniently in the form of an infusion so that between 5 and 250 mg/Kg of L-NMMA is administered per day. L-NMMA may also be administered by intravenous bolus in which case the maximum dose per bolus is 20 mg/Kg and preferably 10 mg/Kg, the total amount of L-NMMA administered by this method in a day will be between 5 and 250 mg/Kg.

The dose of the NO synthase inhibitor will vary according to the potency of the inhibitor, its selectivity for the inducible form of the enzyme and the dose at which adverse pharmacological effects become evident. The man skilled in the art will take these factors into account when determining the dose of inhibitor to be administered.

EXAMPLE

Male Wistar-Kyoto rats (250–300 g) were starved and given distilled water to drink for 24 h before the experiment. Rats were anaesthetized with sodium thiobutabarbital (Inactin, 100 mg/kg i.p.) and placed on a heating pad to maintain body temperature at 37° C. A tracheotomy was performed and the animals were ventilated with room air. A pressure transducer (Elcomatic EM750) was connected via a cannula containing heparinized saline (10 U/ml) to the left carotid artery for measurement of blood pressure. A catheter was implanted in the tail vein for administration of drugs. Arterial blood pressure and heart rate were recorded on a four channel polygraph (Grass model 7D).

Following surgery, a period of at least 30 min was allowed for stabilisation of these parameters. After injection of endotoxin; (LPS (4–10 mg/kg, i.v.) blood pressure and heart rate were recorded for 5 h. Every hour, 1 ml blood samples were withdrawn and the volume replaced with saline via the cannulated carotid artery. Plasma was immediately separated by centrifugation (14,000 x g, 1 min).

Alanine amino transferase (ALT) and creatinine, markers of tissue damage, were determined in plasma by standard methods. Plasma samples were deproteinized by ultrafiltration (Centrifree micropartition system, Amicon) and the $NO_3^-$ in the plasma and urine samples was reduced to $NO_2^-$ with nitrate reductase in incubates containing nitrate reductase (20 mU), phosphate buffer (1.2 M, pH 7.5), FAD (120 mM) and NADPH (14.4 mM) and 100 µl of deproteinized plasma to give a final volume of 120 µl. Samples were incubated for 1 h at 37° C. after which a 5–10 µl aliquot was injected into a reaction vessel containing 6% aqueous sodium iodide/glacial acetic acid (1:5, v/v) under reflux, Under these conditions $NO_2^-$ is reduced to NO, which reacts with ozone to form a chemiluminescent product. A standard curve of reduction of $NO_3^-$ to $NO_2^-$ was performed in each experiment as a reference. As plasma and urine contain both $NO_2^-$ and $NO_3^-$ the concentrations are reported as total $NO_2^-/NO_3^-$.

Materials

Endotoxin (S. typhosa LPS, Difco), L-NMMA (Wellcome), L-norepinephrine bitartrate (Koch-Light Laboratories), sodium thiobutabarbital (Inactin, Byk Guilden), nitrate reductase (Sigma), FAD (Sigma) and NADPH tetrasodium salt (Boehringer Mannheim) were obtained as indicated.

Statistics

Results are expressed as the mean ± standard error of the mean for n experiments. Student's unpaired t-test was used to determine statistical significance and $p<0.05$ was considered statistically significant.

RESULTS

Anaesthetized rats, not treated with LPS, showed a small fall in blood pressure (19±5%) accompanied by an increase in plasma creatinine and urea levels (31±8 and 28±4% respectively; $P<0.05$) 6 h after surgery. There was no significant change in the levels of ALT in plasma (FIG. 1) or in $NO_2^-/NO_3^-$ in plasma or urine (not shown), and none of the animals died during the course of the experiment (n=7).

Administration of LPS (4–10 mg/kg i.v.) caused an initial transient (<40 min) fall (not shown) followed by a sustained decline in blood pressure over the next 5 h (64±7%; FIG. 1). This was accompanied by increases in plasma $NO_2^-/NO_3^-$, creatinine and ALT, which were significant 2 h after administration of LPS (FIG. 1); 37% (7/19) of these animals died between 4 and 5 h after administration of LPS.

Administration of a continuous infusion of norepinephrine, at doses sufficient to maintain blood pressure at control levels (300–500 µl/kg/h), prevented the fall in blood pressure up to 3 h, without affecting the increase in plasma $NO_2^-/NO_3^-$, creatinine or ALT (FIG. 2). There was no improvement in the mortality of this group of animals compared to those treated with LPS alone.

Bolus administration of L-NMMA (3–300 mg/kg, i.v.) 90 min after LPS caused a dose-dependent rise in blood pressure within 5 min of administration. The duration of this rise was also dose-dependent, lasting for between 8 and 200 min, except for the highest dose of L-NMMA in which the rise in blood pressure was rapidly followed by a precipitous fall in blood pressure and death. A low dose of L-NMMA (3 mg/kg) caused a short-lasting (<10 min) increase in blood pressure without affecting its subsequent fall or the rise in plasma creatinine or mortality (FIG. 4). Plasma $NO_2^-/NO_3^-$ levels were reduced significantly at 2 and 3 h, but not subsequently and there was a reduction in plasma ALT at 2 h but not at subsequent time points (FIG. 3).

Intermediate doses of L-NMMA (10 and 30 mg/kg) induced increases in blood pressure for 17±3 and 56±16 min respectively and prevented the fall in blood pressure observed in animals treated with LPS alone (FIG. 3). Plasma $NO_2^-/NO_3^-$, creatinine and ALT levels were reduced significantly at all times by both doses of L-NMMA and none of the animals in these groups died.

Higher doses of L-NMMA (100 and 300 mg/kg i.v.) increased blood pressure for up to 150 min and 90 min respectively, after which there was a rapid fall, which in the case of 300 mg/kg was greater than that induced by LPS alone (FIG. 3). These doses of L-NMMA inhibited significantly the rise in plasma $NO_2^-/NO_3^-$; but potentiated the increase in plasma ALT at later times. Both these doses of L-NMMA tended to increase the death rate, such that 4 out of 7 (57%) and 7 out of 10 (70%) animals, respectively, died by the end of the experiment.

DISCUSSION

Administration of LPS to anaesthetized rats caused a progressive decline in blood pressure, which was accompanied by an increase in creatinine and ALT in the plasma, and the death of some of the animals. The level of creatinine and ALT in the plasma are an indication of the number of cells dying in the body. All these changes occurred over a similar time-course and are characteristic of endotoxin shock in animals and humans.

The development of these signs and symptoms of endotoxin shock was accompanied by a progressive rise in plasma $NO_2^-/NO_3^-$, which was significant after 2 h. A similar rise in $NO_2^-/NO_3^-$ in urine indicates that it is not attributable to reduced excretion as a result of compromised renal function during the development of the shock.

The fall in blood pressure, but not the increase in plasma $NO_2^-/NO_3^-$, was attenuated for up to 3 h by administration of norepinephrine (noradrenaline), which is the current method of clinical management of septic shock. However, there was no change in the levels of creatinine, ALT or survival, suggesting that improvements in blood pressure are not sufficient to counteract tissue damage and mortality in shock.

The fall in blood pressure induced by LPS was not affected significantly by a low dose (3 mg/Kg) of L-NMMA which did however inhibit significantly the increase in $NO_2^-/NO_3^-$ and the increase in ALT 30 min after administration of the drug. In contrast, higher doses (10 and 30 mg/Kg) of L-NMMA prevented the fall in blood pressure induced by LPS and increased the survival of the animals. Our finding that L-NMMA caused a reduction in tissue damage suggests that tissue damage is NO-related. This proposal is supported by the cytotoxic effect that follows the induction of NO synthesis in vascular endothelial cells with LPS and the finding that maintenance of blood pressure with norepinephrine did not prevent tissue damage.

Higher doses of L-NMMA (100 and 300 mg/kg) which attenuate $NO_2^-/NO_3^-$ synthesis at all times, induced a more pronounced increase in blood pressure, rapidly followed by a sharp fall, which was accompanied by a rise in plasma ALT and enhanced mortality.

Figure 1:
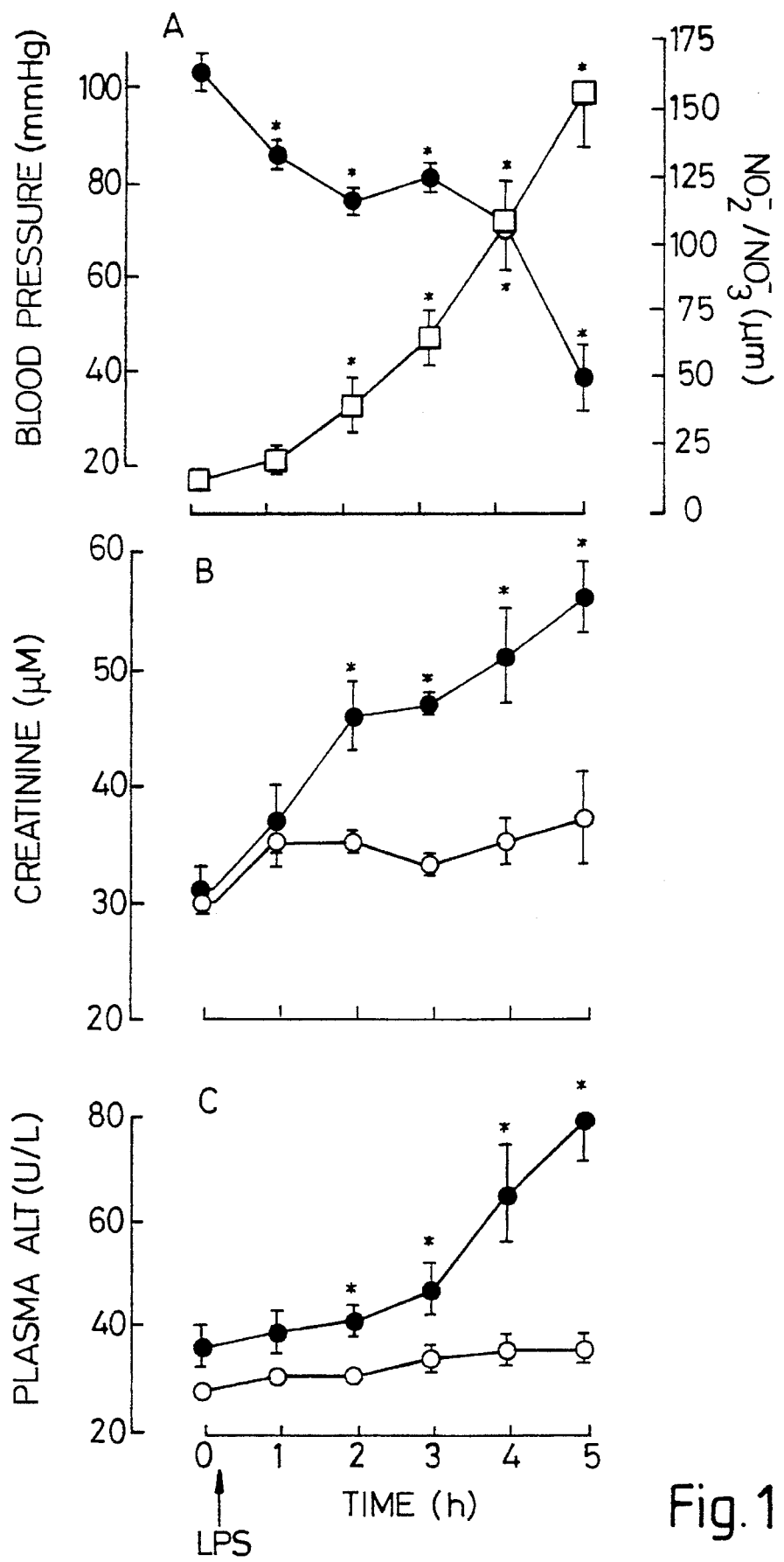
FIG. 1 Changes in blood pressure, $NO_2^-/NO_3^-$, creatinine and ALT after administration of LPS. A. Intravenous administration of LPS (4 mg/kg) causes a progressive fall in blood pressure (●) accompanied by an increase in $NO_2^-/NO_3^-$ (□). B. Time-dependent increase in plasma creatinine after administration of LPS (●); untreated control (o). C. Time-dependent increase in plasma ALT after administration of LPS (●); untreated control (o). Each point is the mean±s.e.m. of 6–12 animals and *indicates significantly different from initial value, $p<0.05$.
Figure 2:
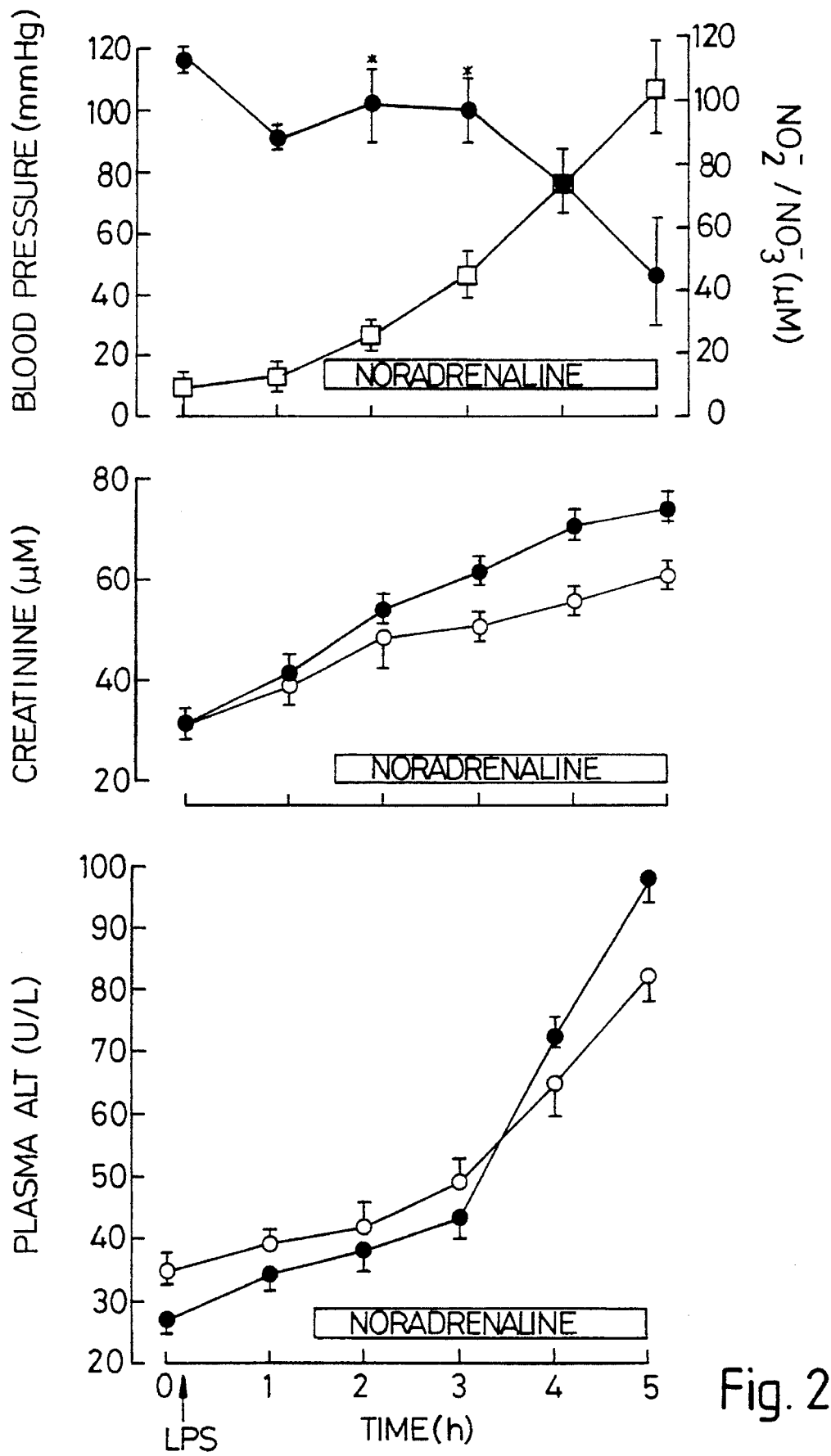
FIG. 2 Effect of a continuous infusion of noradrenaline on blood pressure, plasma $NO_2^-/NO_3^-$, creatinine and ALT. Infusion of noradrenaline (●) prevented the fall in blood pressure induced by LPSup to 3 h, after which there was a progressive decline. Increasing the dose of norepinephrine further at this point was not able to maintain the blood pressure (not shown). There was no significant difference in the rise in plasma $NO_2^-/NO_3^-$, creatinine or ALT compared to animals treated with LPS alone (o). Each point is the mean±s.e.m. of 6 animals and * indicates $p<0.05$ compared to LPS alone.
Figure 3:
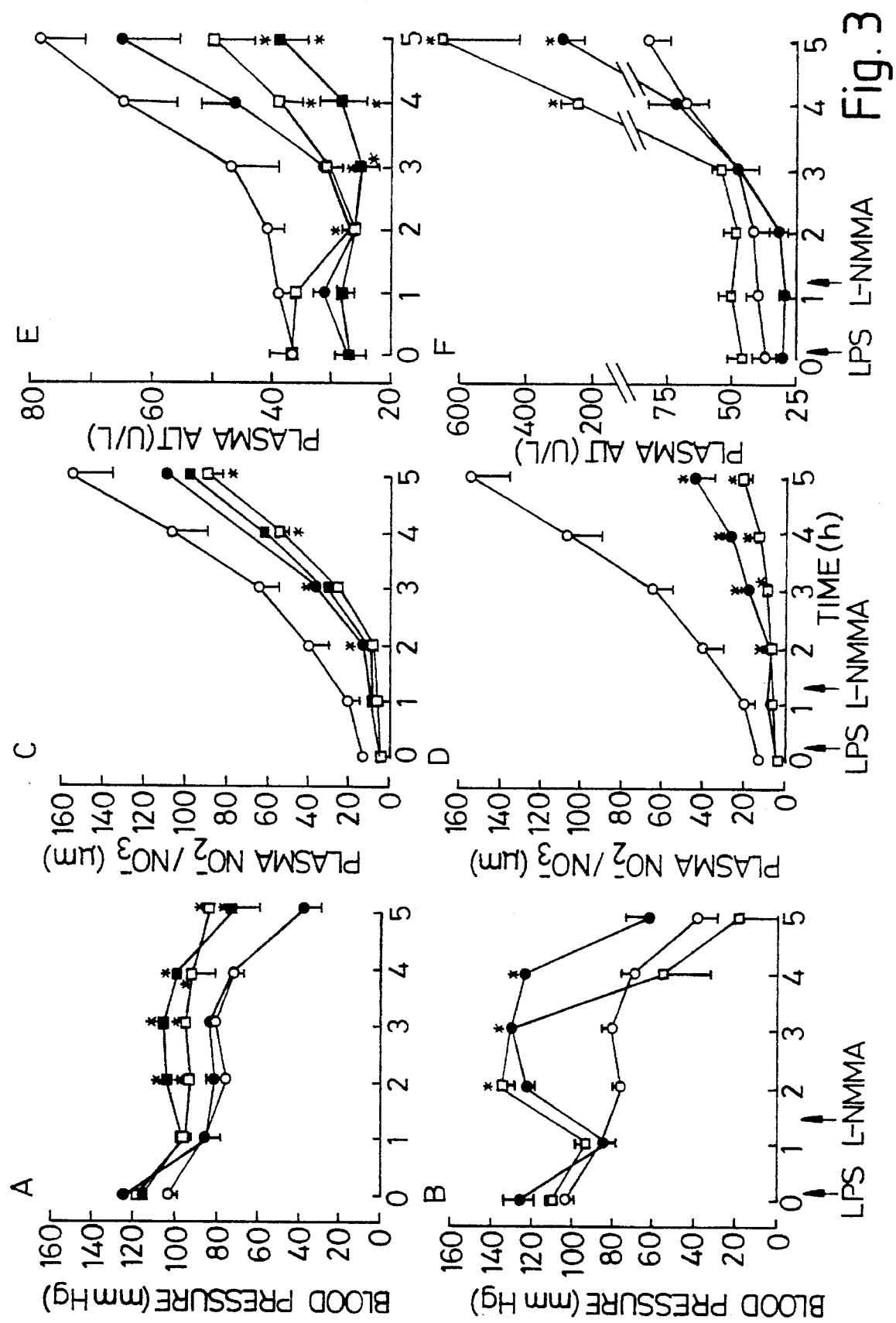
FIG. 3 Effect of L-NMMA on blood pressure, plasma $NO_2^-/NO_3^-$ and ALT. A. L-NMMA (3 mg/kg; ●) had no significant effect on the fall in blood pressure induced by LPS (o). At 10 mg/kg (□) and 30 mg/kg (■), L-NMMA prevented the fall in blood pressure. B. Higher doses of L-NMMA (100 mg/kg (●) and 300 mg/kg (□) caused a sustained increase in blood pressure, before causing a sharp fall at later times. The late fall in blood pressure induced by L-NMMA at 300 mg/kg was significantly greater and occurred earlier than that caused by 100 mg/kg. C. D. The rise in plasma $NO_2^-/NO_3^-$ induced by LPS (o) was significantly inhibited by all doses of L-NMMA (see above for symbols). E. The rise in plasma ALT induced by LPS (o) was significantly inhibited by lower doses of L-NMMA. F. Higher doses (100 mg/kg and 300 mg/kg; ●, □) significantly potentiated the increase in ALT at the 4 and 5 h time points. Each point is the mean±s.e.m. of 5–8 animals and *indicates $p<0.05$ compared to LPS alone.

We claim:

1. A method for inhibiting tissue damage involving the disruption or death of cells in a mammal in the absence of hypotension in said mammal and having a condition causing pathological NO production, which comprises administering to a mammal in need thereof an effective tissue damage inhibition amount of a NO synthase inhibitor.

2. A method for inhibiting tissue damage according to claim 1 wherein the pathological NO production is caused by septicaemia.

3. A method for inhibiting tissue damage according to claim 1 wherein the pathological NO production is caused by inflammatory conditions.

4. A method for inhibiting tissue damage according to claim 1 wherein the pathological NO production is caused by immunological reactions.

5. A method of inhibiting tissue damage involving the disruption or death of cells in a mammal having a fungal, protozoal or viral infection and in need thereof comprising administering an effective tissue damage inhibition amount of NO synthase inhibitor to said mammal.

6. A method of inhibiting tissue damage involving the disruption or death of cells in a mammal having a bacterial infection which comprises administering to a mammal in need thereof an NO synthase inhibitor in an amount sufficient to limit increases in ALT and creatinine levels due to cell death.

7. A method of inhibiting tissue damage involving the disruption or death of cells in ARDS or myocarditis in a mammal in need thereof which comprises administering to a mammal in need thereof an effective amount of an NO synthase inhibitor.

8. The method of any one of claims 1 to 7 in which the NO synthase inhibitor is L-NMMA.

* * * * *